(12) United States Patent
Shukla

(10) Patent No.: US 8,170,319 B2
(45) Date of Patent: May 1, 2012

(54) MOTION DETECTION BY DIRECT IMAGING DURING RADIOTHERAPY

(75) Inventor: Himanshu P. Shukla, Lafayette, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 888 days.

(21) Appl. No.: 12/205,608

(22) Filed: Sep. 5, 2008

(65) Prior Publication Data

US 2010/0061515 A1    Mar. 11, 2010

(51) Int. Cl.
*A61N 5/10* (2006.01)
(52) U.S. Cl. .............................. 382/132; 382/131; 378/65
(58) Field of Classification Search .................... 378/20, 378/65; 382/131, 132
See application file for complete search history.

(56) References Cited

U.S. PATENT DOCUMENTS

| | | | |
|---|---|---|---|
| 5,784,431 A | 7/1998 | Kalend et al. | |
| 5,901,199 A * | 5/1999 | Murphy et al. | 378/65 |
| 6,118,848 A * | 9/2000 | Reiffel | 378/65 |
| 6,307,914 B1 * | 10/2001 | Kunieda et al. | 378/65 |
| 6,516,046 B1 * | 2/2003 | Frohlich et al. | 378/65 |
| 6,865,253 B2 * | 3/2005 | Blumhofer et al. | 378/65 |
| 6,865,254 B2 * | 3/2005 | Nafstadius | 378/65 |
| 6,942,618 B2 | 9/2005 | Simopoulos | |
| 7,154,991 B2 * | 12/2006 | Earnst et al. | 378/65 |
| 7,212,608 B2 * | 5/2007 | Nagamine e | 378/65 |
| 7,221,733 B1 * | 5/2007 | Takai et al. | 378/65 |
| 7,227,925 B1 * | 6/2007 | Mansfield et al. | 378/65 |
| 7,289,599 B2 * | 10/2007 | Seppi et al. | 378/65 |
| 7,412,029 B2 * | 8/2008 | Myles | 378/65 |
| 7,415,095 B2 * | 8/2008 | Wofford et al. | 378/65 |
| 7,453,984 B2 * | 11/2008 | Chen et al. | 378/65 |
| 7,460,640 B2 * | 12/2008 | Kamikonya et al. | 378/65 |
| 7,623,623 B2 * | 11/2009 | Raanes et al. | 378/65 |
| 7,664,226 B2 * | 2/2010 | Hui et al. | 378/65 |
| 7,672,429 B2 * | 3/2010 | Urano et al. | 378/65 |
| 7,853,308 B2 * | 12/2010 | Sauer et al. | 600/425 |
| 7,945,021 B2 * | 5/2011 | Shapiro et al. | 378/65 |
| 2006/0002615 A1 | 1/2006 | Fu et al. | |
| 2006/0002630 A1 | 1/2006 | Fu et al. | |
| 2006/0074299 A1 | 4/2006 | Sayeh | |

FOREIGN PATENT DOCUMENTS

JP    9065195 A    3/1997

OTHER PUBLICATIONS

Ross I. Berbeco et al., "Towards fluoroscopic respiratory gating for lung tumours without radiopaque markers", Phys. Med. Biol. 50, (2005), Institute of Physics Publishing, Physics in Medicine and Biology, pp. 4481-4490 (9pgs total).

Ying Cui et al., "Robust fluoroscopic respiratory gating for lung cancer radiotherapy without implanted fiducial markers", Phys. Med. Biol. 52, (2007), Institute of Physics Publishing, Physics in Medicine and Biology, pp. 741-755 (15pgs total).

\* cited by examiner

*Primary Examiner* — Allen C. Ho

(57) ABSTRACT

An apparatus, method, system, and means to detect motion of a subject by direct imaging on a treatment plane during a radiotherapy treatment, the method includes delivering a radiotherapy treatment beam to a volume of interest of the subject during a treatment time, acquiring image data during the treatment time associated with the delivery of the radiotherapy treatment beam by a direct imaging of a projection of the treatment volume of interest, providing a real-time display of the acquired image data, determining the occurrence of a motion in the volume of interest during the treatment time, determining the motion exceeds a pre-determined threshold, and outputting an indication the determined motion exceeds the pre-determined threshold during the treatment time.

19 Claims, 3 Drawing Sheets

200

```
┌─────────────────────────────────────────────────┐
│ DELIVER A RADIOTHERAPY TREATMENT BEAM TO A VOLUME OF │
│ INTEREST OF A SUBJECT DURING A TREATMENT TIME   │
│                                             205 │
└─────────────────────────────────────────────────┘
                        ↓
┌─────────────────────────────────────────────────┐
│ ACQUIRE IMAGE DATA DURING THE TREATMENT TIME    │
│ ASSOCIATED WITH THE DELIVERY OF THE             │
│ RADIOTHERAPY TREATMENT BEAM BY A DIRECT IMAGING │
│ OF A PROJECTION OF THE TREATMENT VOLUME OF INTEREST │
│                                             210 │
└─────────────────────────────────────────────────┘
                        ↓
┌─────────────────────────────────────────────────┐
│ PROVIDE A REAL-TIME DISPLAY OF THE              │
│ ACQUIRED IMAGE DATA                             │
│                                             215 │
└─────────────────────────────────────────────────┘
                        ↓
┌─────────────────────────────────────────────────┐
│ DETERMINE THE OCCURRENCE OF A MOTION IN THE     │
│ VOLUME OF INTEREST DURING THE TREATMENT TIME    │
│                                             220 │
└─────────────────────────────────────────────────┘
                        ↓
┌─────────────────────────────────────────────────┐
│ DETERMINE THE MOTION EXCEEDS A                  │
│ PRE-DETERMINED THRESHOLD                        │
│                                             225 │
└─────────────────────────────────────────────────┘
                        ↓
┌─────────────────────────────────────────────────┐
│ OUTPUT AN INDICATION THE DETERMINED MOTION      │
│ EXCEEDS THE PRE-DETERMINED THRESHOLD            │
│ DURING THE TREATMENT TIME                       │
│                                             230 │
└─────────────────────────────────────────────────┘
```

MOTION DETECTION BY DIRECT IMAGING DURING RADIOTHERAPY

BACKGROUND

1. Field

The embodiments described below relate generally to imaging using radiation. More particularly, some embodiments concern acquiring an image during a radiotherapy treatment to using the treatment radiation to determine a motion in an area of interest of a subject.

2. Description

Images of internal patient volumes are commonly used in modern medical practice. Such images may be used to generate or confirm a diagnosis and/or to plan a course of treatment. In order to obtain an internal image, a patient is typically irradiated with one or more imaging beams of radiation prior to a treatment session. Images obtained prior to the current treatment session may also be used to aid patient positioning immediately prior to an administration of the radiotherapy treatment.

An important aspect of radiotherapy treatment concerns positioning the subject in the proper location to ensure the accurate delivery of radiation during the treatment session. Conventionally, the volume(s) of interest that will be irradiated during a treatment session are imaged prior to the treatment irradiation in order to accurately ascertain their location within the subject. Disadvantages related to this method, as a sole approach, is the lack of information regarding patient and target information once treatment radiation has been initiated. Thus, it is usually a prescribed protocol only for patient set-up.

In some aspects, treatment radiation may be serially delivered from different angles. Thus, knowledge of patient and target location integrity may be valuable during one of more treatment trajectories. As opposed to utilizing an imaging system stationary to the patient, imaging of the treatment beam offers the most direct form of information regarding the beam/patient relationship.

SUMMARY

To address at least the foregoing, some embodiments provide a system, method, apparatus, and means including direct imaging of a treatment volume of interest. In some embodiments, a method includes delivering a radiotherapy treatment beam to a volume of interest of a subject during a treatment time (i.e., a "beam-on time" of the treatment beam), acquiring image data during the treatment time associated with the delivery of the radiotherapy treatment beam by a direct imaging of a treatment volume of interest, providing a real-time display of the acquired image data, determining the occurrence of a motion in the volume of interest during the treatment time, determining the motion exceeds a pre-determined threshold, and outputting an indication the determined motion exceeds the pre-determined threshold during the treatment time.

In further aspects, the acquiring of the image data during the treatment time associated with the delivery of the radiotherapy treatment beam by direct imaging includes acquiring the image data in a plane orthogonal to the radiation beam associated of the radiotherapy treatment.

In some embodiments, the delivery of the radiotherapy treatment beam in response to a determination that the determined motion exceeds a pre-determined threshold may include modifying the radiotherapy treatment and its progress, where the modification may include a manually invoked response and an automatically invoked response.

In some instances, the determining the occurrence of a motion in the volume of interest during the treatment time is based on a self-consistent comparison of anatomy in at least some of the acquired image data to prior images acquired during treatment time.

In some instances, the determining of the occurrence of a motion in the volume of interest during the treatment time is based on a comparison of anatomy in at least some of the acquired data images and at least one reference image acquired prior to initiation of the treatment time.

In some aspects, a system may carry out the methods herein. The system may include a radiation source to emit a radiotherapy treatment beam during a radiotherapy treatment session to a volume of interest of a subject during a treatment time, a radiation image detector to acquire image data based on at least a portion of the emitted treatment beam passing through the volume of interest of the subject during the treatment time and impinging on the radiation image detector, and a processor. The processor may be operative to generate, in real-time, an image of the acquired image data, determine the occurrence of a motion in the volume of interest during the treatment time, determine the motion exceeds a pre-determined threshold, and output an indication the determined motion exceeds the pre-determined threshold during the treatment time.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein:

FIG. 2 is an exemplary flow diagram, relating to some embodiments herein; and

DETAILED DESCRIPTION

The following description is provided to enable any person in the art to make and use the described embodiments and sets forth the best mode contemplated by for carrying out some embodiments. Various modifications, however, will remain readily apparent to those in the art.

A method and system is presented for tracking motion in a treatment target during the time of delivery of a radiotherapy treatment, without a need for non-native imaging reference structures (e.g., fiducial markers) prior to the treatment.

In the following description, for purposes of explanation, numerous specific details are set forth in order to provide an understanding of the present disclosure. It will be evident, however, to one skilled in the art that aspects of the present disclosure may be practiced without these specific details. In some embodiments, well-known structures and devices are shown in block diagram form, rather than in detail, in order to avoid obscuring the present disclosure. These embodiments are described in sufficient detail to enable those skilled in the art to practice the invention, and it is to be understood that other embodiments may be utilized and that logical, mechanical, electrical and other changes may be made without departing from the scope of the present invention.

Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

As used herein, the term "treatment session" refers to a group of treatment beam trajectories desired for delivery in a single treatment appointment. All of the treatment appointments comprising a particular course of treatment are referred to as a radiotherapy course.

As used herein, a "treatment time" refers to the time that a treatment beam is actually on for the purpose of delivering a prescribed treatment radiation. Accordingly, the treatment time is associated with a delivery of a radiotherapy treatment beam.

Figure 1:
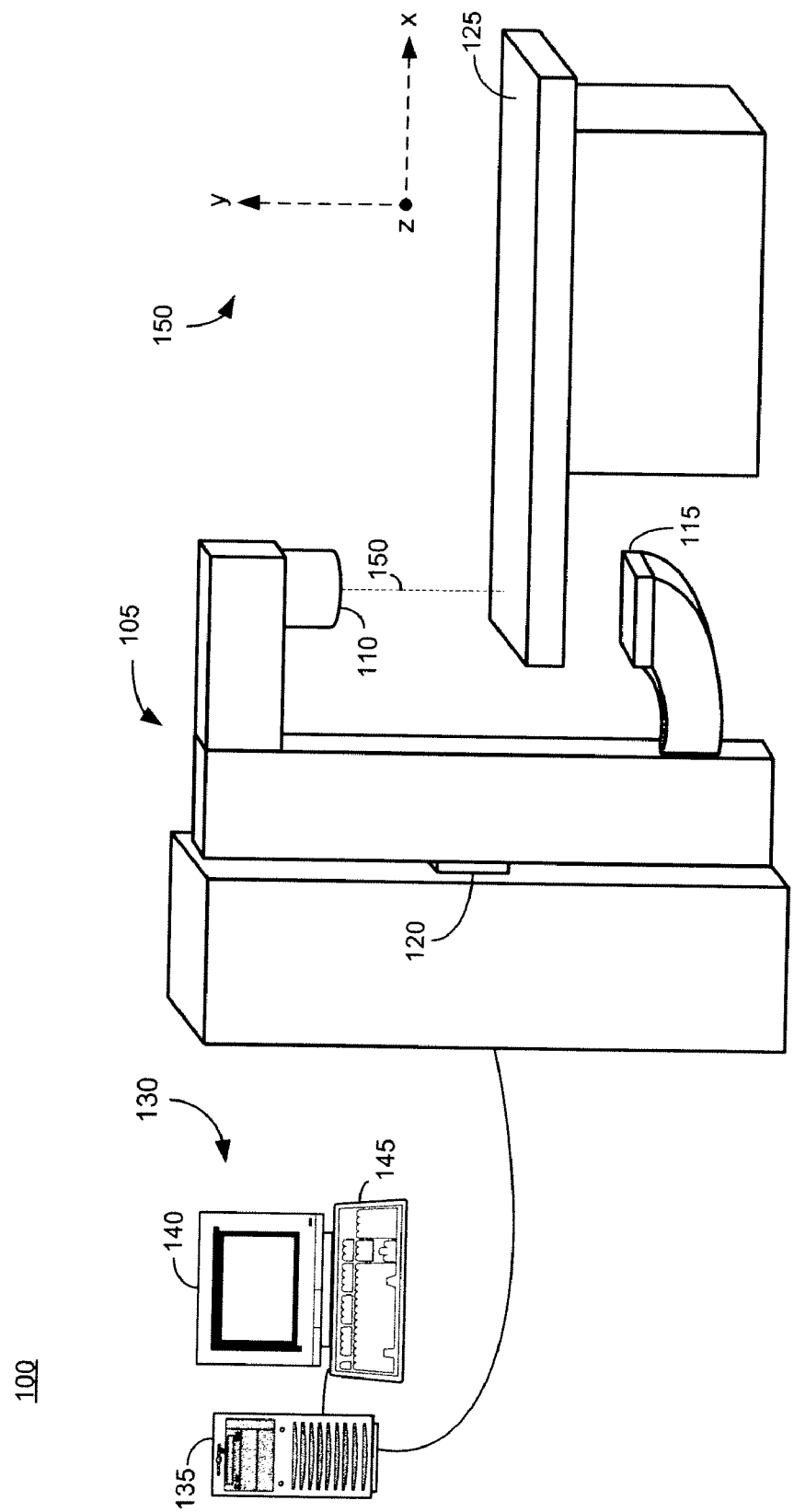
FIG. 1 is a diagram illustrating aspects of a radiotherapy treatment and imaging system, according to some embodiments herein.

FIG. 1 illustrates a radiotherapy treatment and imaging system 100, according to some embodiments. System 100 includes a gantry 105 having a radiation source 110 and a radiation image detector 115 to detect radiation emitted from the radiation source. Radiation source 110 emits radiation during the course of a radiotherapy treatment session according to a treatment plan. Radiation source 110 may comprise any suitable type of radiation. In some aspects, the radiation source may emit a treatment beam of, for example, megavolt radiation. A bed 125 is provided to position a subject (not shown), such as a human undergoing radiotherapy treatment and/or imaging to a particular body part (i.e., a volume of interest), in an area between radiation source 110 and radiation detector 115. Gantry 105 may be rotated about a pivot point 120 in order to image a subject on bed 125 from a variety of angles to facilitate comprehensive imaging, including the acquisition of projection images used to generate two-dimensional (2-D) and three-dimensional (3-D) images before initiating treatment.

In some embodiments, a computer system or processor 130 may be interfaced to or included with system 100 to control the operation of system 100. In some embodiments, a computer system or processor 130 may be interfaced or included with system 100 to control a sequence of operations related to the delivery of radiotherapy and the processing of image data generated and acquired by system 100. System 100 may be operated to control or direct a delivery of a treatment beam to a subject located on table 125, detect radiation impinging on radiation detector 115 that has passed through the subject to acquire image data, produce time-consecutive 2-D images, and further process the image data to determine whether there is an occurrence of motion in a volume of interest in the subject while undergoing the radiotherapy treatment.

Computer system 130 may include a processing unit 135 having a processor (not shown) and a memory (not shown). The processing functionality and memory of processing unit 135 may be implemented in one or more systems and devices, whether locally, remotely, or across a distributed computing environment. The memory may store instructions, process steps, and code thereon that may further be executed by the processor of processing unit 135. The instructions, process steps, and code may comprise methods, processes, and operations corresponding to the methods and processed disclosed herein. System 130 further includes a display unit 140 to display, for example, images acquired in real-time during a radiography treatment, in accordance herewith. System 130 may also include a data entry device such as, for example, keyboard 145. Keyboard 145 may be used by an operator to invoke, pause, terminate, and otherwise direct or control certain operation of system 100. System 100 may include devices capable of providing an aural or visual alert to the operator such as, for example, a speaker system, alert monitor, etc.

In some aspects, the present invention can be implemented by an apparatus for performing the operations and processes herein. This apparatus may be specially constructed for the required purposes, or it may comprise a general purpose computer, selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

Various general purpose systems may be used with programs in accordance with the teachings herein, or it may prove convenient to construct more specialized apparatus to perform the required method. For example, any of the methods or parts thereof according to the present disclosure may be implemented in hard-wired circuitry, by programming a general purpose processor or by any combination of hardware and software. One of skill in the art will appreciate that the present disclosure may be practiced with computer system configurations other than those described below, including multiprocessor systems, network PCs, minicomputers, mainframe computers, and the like. The invention can also be practiced in distributed computing environments where tasks are performed by remote processing devices that are linked through a communications network.

It should be appreciated that a hardware and/or software environment according to some embodiment may include fewer, more, and other components than those specifically depicted in FIG. 1. That is, embodiments are not limited to radiotherapy treatment systems depicted herein.

The particular treatment beam radiation (e.g., beam shape, intensity, duration, frequency, etc.) emitted from radiation source 110 may depend on, for example, the goal of a treatment session and the particular area of interest to be imaged. In some embodiments, radiation detector 115 detects the radiation passing through the subject (not shown) and incident on the radiation detector and generates image data corresponding to the location and intensity of the radiation incident thereupon. In some embodiments, radiation detector 115 may comprise a flat panel device (FPD). FPD 115 may include any suitable detector material, device, or system capable of detecting radiation from radiation source 110. In some embodiments, FPD 115 may include a scintillator to convert radiation incident thereupon to visible light of a corresponding intensity. The light generated by the scintillator may subsequently be converted to electrical signals in a detector 115 array of pixel elements. Those skilled in the art of the present disclosure will recognize that the materials and devices of radiation detector may be adapted to accommodate the particular type and intensity of radiation delivered during a radiography treatment time, as well as other factors such as desired image clarity, contrast, and detail.

The dimensions of the projection images generated by system 100 may be similar to the dimensions of FPD 115, including the array of pixilated elements therein. Referring to the FIG. 1, coordinate system 150 illustrates a beam perspective of table 125, wherein the illustrated y-direction is directed from the radiation isocenter of system 100 towards gantry 105, the illustrated x-direction points from the isocenter towards the right of gantry 105 when facing the gantry, and the z-direction is directed upwards from the isocenter. Table 125 may be moved in the z-direction to place a different portion of a subject 15 within a treatment plane between radiation source 110 and radiation detector 115.

In accordance with the present disclosure, a radiation treatment beam is used for treatment of the subject and imaging of the subject. Accordingly, in embodiments, the imaging plane of the radiation detector 115 (e.g. a FPD) is maintained orthogonally with respect to a radiation treatment beam 150 emitted from radiation source 110 during a radiotherapy treatment session. Correspondingly, images of the subject provided by system 100 and in accordance with methods herein are in the radiation detector plane (x-y plane) orthogonal to the treatment beam direction. Accordingly, motion detection may be detected and determined in the plane orthogonal to the treatment beam direction directly. Such motion may provide some of the most relevant components of subject object perturbation.

FIG. 2 illustrates a flow diagram of a process 200, in accordance with some aspects herein. Aspects of process 200 may be implemented, in whole or in part, by hardware and software, either alone or in combination including, but not limited to, system 100. At operation 205, a radiotherapy treatment session is commenced to deliver a radiotherapy treatment beam (i.e., radiation) to a volume of interest of a subject such as a human or veterinary patient. It will be appreciated that prior to the delivery of the treatment, the data acquisition system discussed herein (e.g., system 100) is deployed and configured in the proper location and positioning relative to the subject for the acquisition of images.

At operation 210, image data is acquired using, for example, FPD 115. In some instances, the image acquisition is gathered at maximum rate, or a rate corresponding to the rate the treatment radiation is executed. In such instances, the acquired data images may be correlated with the parallel treatment sequences. Accordingly, the images acquired by the image acquisition system are consistent and aligned with the treatment radiation. The need to correlate or compensate for any offsets between a treatment delivery system and a data acquisition system are avoided by the treatment and image data acquisition system herein.

At operation 215, the acquired image data is provided to a display for viewing. In some embodiments, the image data is provided to the display in real-time (i.e., as it is acquired at about, for example, 7 frames per second according the imaging rate on some current treatment systems). The images are displayed in real-time such that an operator, clinician, or other personnel may monitor the progress of the treatment delivery via image acquisition herein.

It will be further appreciated that image processing may be performed on the acquired image data in order, for example, to apply calibrated corrections, to filter the acquired image data prior to using the acquired image data for motion determinations and/or display, and to format the image data for display by a display monitor. Image artifacts due to, for example, asynchronous characteristics or interference (if any) due to the simultaneous delivery and treatment of radiation, may be accomplished using one or more processes, algorithms, and techniques. In some embodiments, the acquired data may be processed to enhance contrast and/or reduce noise anomalies (if any) using any now known or future known processes, algorithms, and techniques.

In some embodiments, the image data processing occurs "on-the-fly" such the acquired data may be filtered for at least some artifacts and/or enhanced for viewing before the acquired data is presented and displayed for viewing by an operator. It is noted that the image processing preferably happens at a rate which does not adversely delay the displaying of the image data to the operator. In some embodiments, the rate of treatment delivery, image data acquisition, and image processing is such that the acquired images are displayed at or very close to the rate at which they treatment is delivered and the images are acquired (e.g., real-time rate of 7 frames per second). In instances where processing may present a bottleneck to near real-time display, image processing algorithms may be simplified and/or implemented in firmware to reduce image processing impediments to near real-time image display.

At operation 220 a determination is made whether a motion has occurred based on an analysis of the acquired image data. Motion detection may be implemented using a number and variety of motion detection processes, techniques, and methods. Motion detecting methods consistent with the present disclosure include, but are not limited to vision-based motion detection processes such as, for example, Principal Component Analysis. The present disclosure is not limited to a particular image analysis process, technique, or method for detecting motion in image data. In an instance where motion detecting processing may present a bottleneck to near real-time determination of motion in an acquired image, motion detecting processing algorithms may be simplified and/or implemented in firmware (or other techniques) to achieve the desired near real-time motion detecting processing.

In some embodiments, the motion is detected based on the images acquired during the current treatment time. That is, no image or reference image of the treatment volume of interest or subject obtained prior to the treatment time is needed for detecting motion in the acquired image data. The treatment time acquired images may be independently used as the basis of determining whether there is any motion in the irradiated volume of interest during the current treatment time.

In some embodiments, a first one or more images acquired during the treatment time a treatment beam is delivered to a subject may be used to establish a basis for comparison with image data acquired later in the treatment time. For example, the first three frames acquired during a treatment time may be averaged to establish a baseline reference for later-acquired images of the same treatment time and used in the determining of whether there is movement in the latter image data.

In some embodiments herein, one or more images acquired during the treatment time may be used in comparison with one or more reference images of the volume of interest that were obtained prior to the treatment time. The images obtained prior may, as an example, be obtained as part of a radiotherapy planning task. During the radiotherapy planning task, the subject positioned in a desired treatment position "simulating" treatment may be used to generate 2-D reference images of selected beam trajectories through the subject. The radiotherapy planning task may include designating an area of interest on the reference images in order to designate corresponding areas to be monitored on images acquired during treatment time. Together, the treatment time acquired image data and the prior reference image data may be used as a basis for comparison for determining whether there is significantly relevant motion in an image acquired during the treatment time.

In some embodiments herein, one or more images acquired during the treatment time may be used in comparison with one or more reference images of the volume of interest that were obtained during a treatment session but before treatment time delivery of the treatment beam. For example, a single static 2D image of the beam shape may be acquired as reference just prior to treatment time for each beam. In such embodiments, there may not be sufficient time to designate an area of interest in the reference images due to the typically limited duration of a treatment appointment (e.g., 15 minutes). In such instances, the entire image may be monitored for a significantly relevant motion since an area of interest has not been designated. Together, the treatment time acquired image data and the prior reference image data may be used as a basis for comparison for determining whether there is significantly relevant motion in an image acquired during the treatment time.

At operation 225, a determination is made to discern whether a detected motion exceeds a pre-determined motion threshold. This operation may provide compensation for the occurrence of some known and/or unavoidable motion(s). For example, it is known that some motion will occur in certain areas of interest, such as the lungs due to respiratory function. Thus, the monitored area of interest may be chosen to avoid confounding motion, or the anticipated regular motion itself may be filtered out of acquired frames by an appropriate algorithm. The motion threshold may be uniquely set on the basis of the selected strategy.

At operation 230, an indication that the detected motion exceeds the pre-determined motion threshold may be provided. The indication may be in the form of any visual, audio, or audio-visual alert, notification, or alarm. In some embodiments, the indication may be provided in more than one format. For example, an audible alarm and a visual icon on a display may be provided in combination. The icon may or may not include a textual description (e.g., amount and direction of the detected motion), a color and/or shape indicative of the type of motion alert or alarm.

Figure 3:
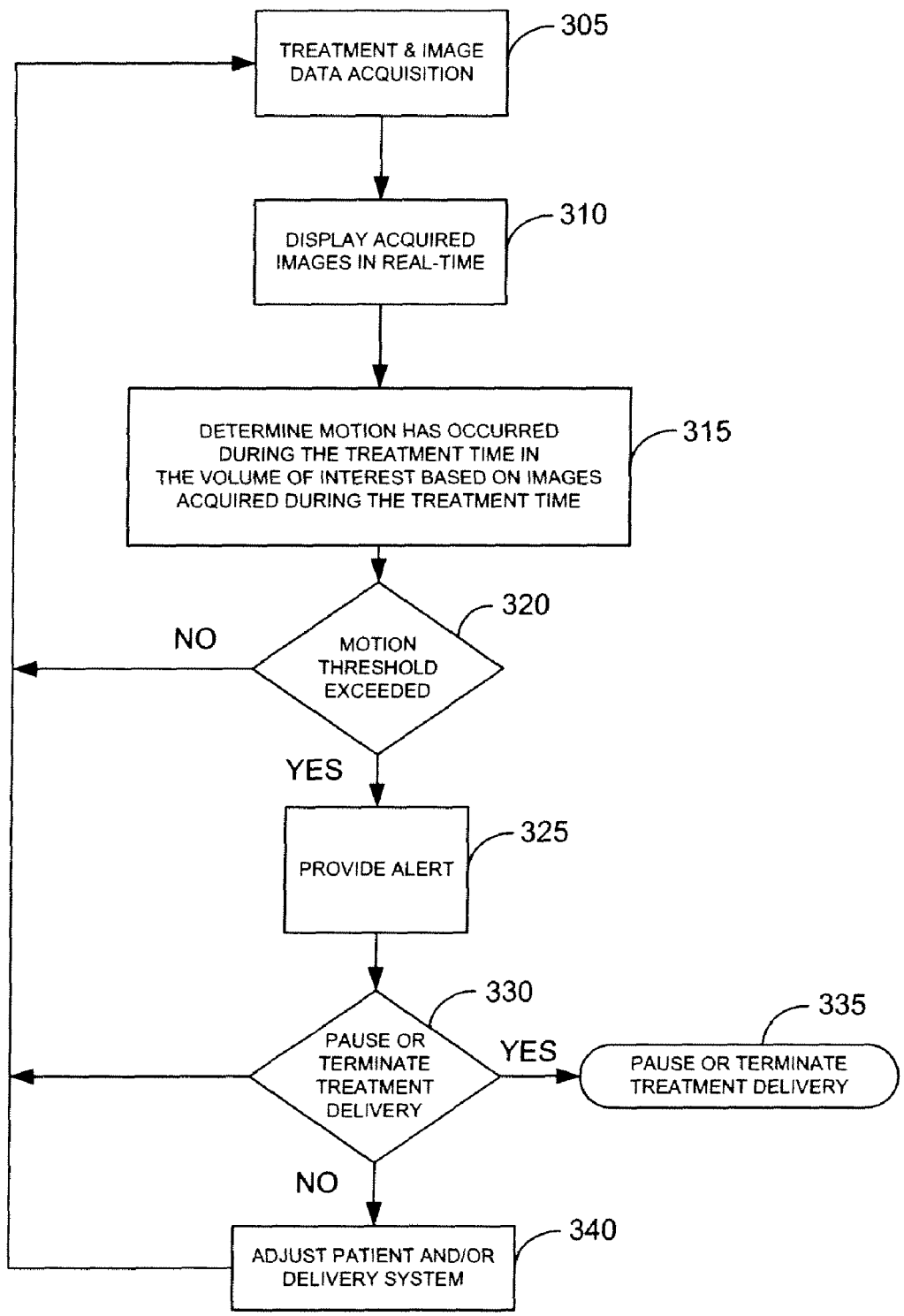
FIG. 3 is yet another exemplary flow diagram, relating to some embodiments herein.

FIG. 3 is an exemplary flow diagram of a process 300, relating to some embodiments. In some aspects, process 300 expands on some of the processes introduced in FIG. 2, process 200. Referring to operation 305, both radiotherapy treatment and image data acquisition are in process, in accordance with the discussion of same herein. At operation 310, images acquired in accordance herewith are displayed in real-time.

At operation 315, process 300 determines a motion has occurred during the treatment time in the volume of interest based on the images acquired during the treatment time. As discussed hereinabove, the determination of whether any motion has occurred during the treatment time as the treatment beam is being administered may be based on the acquired images independently or complementary to reference image(s) obtained prior to the treatment time.

Process 300 proceeds to operation 320 to determine whether a pre-determined motion threshold is exceeded based on the motion determination of operation 315. In the event it is determined the detected motion does not exceed the motion threshold, process 300 continues to operation 305 wherein the treatment delivery and image data acquisition continues. The determined motion in this instance may be within a tolerable variance (i.e., not significantly relevant).

In the event it is determined the determined motion exceeds the motion threshold (i.e., significantly relevant), the process flow continues to operation 325 wherein an alert is provided to a treatment observer, provider, clinician, or other personnel.

In response to the alert condition of operation 325, process 300 may then proceed to operation 330 where the treatment delivery and the dependent direct parallel image data acquisition may be halted or interrupted at operation 335. Treatment delivery along with image data acquisition may be stopped or paused at operation 340 in order to make an adjustment to the subject and/or delivery system. Alternatively, it may be observed by the treatment observer, provider, clinician, or other qualified personnel that the treatment and image data acquisition may continue, process 300 may therefore continue to operation 305 wherein the treatment delivery and image data acquisition continues.

In some embodiments, the response to the alert provided at operation 325 may be invoked automatically by a machine or device comprising or interfaced with the treatment delivery and image data acquisition system (e.g., system 100). In some other instances, the response to the alert provided at operation 325 may be invoked manually by, for example, the treatment observer, provider, clinician, or other qualified personnel.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    delivering a radiotherapy treatment beam to a volume of interest of a subject during a treatment time;
    acquiring image data based on the delivery of the radiotherapy treatment beam during the treatment time associated with the delivery of the radiotherapy treatment beam by a direct imaging of a projection of the treatment volume of interest;
    providing a real-time display of the acquired image data during the treatment time;
    determining an occurrence of a motion in the volume of interest during the treatment time;
    determining the motion exceeds a pre-determined threshold; and
    outputting an indication the determined motion exceeds the pre-determined threshold during the treatment time.

2. The method of claim 1, wherein the acquiring of image data during the treatment time associated with the delivery of the radiotherapy treatment beam by a direct imaging includes acquiring the image data in a plane orthogonal to the radiotherapy treatment beam.

3. The method of claim 1, wherein the radiotherapy treatment beam includes a megavoltage treatment beam.

4. The method of claim 1, further comprising modifying at least one of the delivery of the radiotherapy treatment beam and the acquiring of the image data in response to the determining the motion exceeds a pre-determined threshold.

5. The method of claim 4, wherein the modification of at least one of the delivery of the radiotherapy treatment beam and the acquiring of the image data is accomplished under the control of one of: a manually invoked response and an automatically invoked response.

6. The method of claim 1, wherein the determining of an occurrence of a motion in the volume of interest during the treatment time is based on a comparison of the image data acquired solely during the treatment time.

7. The method of claim 1, wherein the determining of an occurrence of a motion in the volume of interest during the treatment time is based on a comparison of at least some of the acquired image data and at least one reference image acquired prior to a treatment session.

8. An apparatus comprising:
a memory storing processor-executable instructions; and
a processor in communication with the memory and operative in conjunction with the stored instructions to:
   deliver a radiotherapy treatment beam to a volume of interest of a subject during a treatment time;
   acquire image data based on the delivery of the radiotherapy treatment beam during the treatment time associated with the delivery of the radiotherapy treatment beam by a direct imaging of the treatment volume of interest;
   provide a real-time display of the acquired image data;
   determine an occurrence of a motion in the volume of interest during the treatment time;
   determine the motion exceeds a pre-determined threshold; and
   output an indication the determined motion exceeds the pre-determined threshold during the treatment time.

9. The apparatus of claim 8, wherein the processor is configured to acquire image data during the treatment time associated with the delivery of the radiotherapy treatment beam by a direct imaging in a plane orthogonal to the radiotherapy treatment beam.

10. The apparatus of claim 8, wherein the radiotherapy treatment beam includes a megavoltage treatment beam.

11. The apparatus of claim 8, wherein the processor is further configured to modify at least one of the delivery of the radiotherapy treatment beam and the acquiring of the image data in response to the determination the motion exceeds a pre-determined threshold.

12. The apparatus of claim 11, wherein the modification of the at least one of the delivery of the radiotherapy treatment beam and the acquiring of the image data is accomplished under the control of one of: a manually invoked response and an automatically invoked response.

13. The apparatus of claim 8, wherein the determining of an occurrence of a motion in the volume of interest during the treatment time is based on a comparison of the image data image acquired solely during the treatment time.

14. The apparatus of claim 8, wherein the determination of an occurrence of a motion in the volume of interest during the treatment time is based on a comparison of at least some of the acquired image data and at least one reference image acquired prior to a treatment session.

15. A system comprising:
a radiation source to emit a treatment beam of radiation during a radiotherapy treatment to a volume of interest of a subject during a treatment time;
a radiation image detector to acquire image data based on at least a portion of the emitted treatment beam of radiation passing through the volume of interest of the subject during the treatment time and impinging on the radiation image detector; and
a processor to:
   generate, in real-time, an image of the acquired image data;
   determine an occurrence of a motion in the volume of interest during the treatment time;
   determine the motion exceeds a pre-determined threshold; and
   output an indication the determined motion exceeds the pre-determined threshold during the treatment time.

16. The system of claim 15, wherein the radiation image detector is configured to acquire image data during the treatment time associated with the delivery of a treatment beam by direct imaging in a projected plane orthogonal to the radiotherapy beam.

17. The system of claim 15, wherein the processor is further configured to modify at least one of the emitting of the radiotherapy treatment beam by the radiation source and the acquisition of image data by the image detector in response to the determining the motion exceeds a pre-determined threshold.

18. The system of claim 15, wherein the determining of an occurrence of a motion in the volume of interest during the treatment time is based on a comparison of the image data image solely acquired during the treatment time.

19. The system of claim 15, wherein the determining of an occurrence of a motion in the volume of interest during the treatment time is based on a comparison of at least some of the image data acquired during the treatment time and at least one reference image acquired prior to a treatment session.

* * * * *